(12) United States Patent
Moulder

(10) Patent No.: US 9,370,663 B2
(45) Date of Patent: Jun. 21, 2016

(54) IMPLANTABLE MEDICAL DEVICE, MEDICAL SYSTEM AND METHOD FOR DATA COMMUNICATION

(71) Applicant: BIOTRONIK SE & CO. KG, Berlin (DE)

(72) Inventor: J. Christopher Moulder, Portland, OR (US)

(73) Assignee: BIOTRONIK SE & CO., KG, Berlin (DE)

( * ) Notice: Subject to any disclaimer, the term of this patent is extended or adjusted under 35 U.S.C. 154(b) by 155 days.

(21) Appl. No.: 14/152,998

(22) Filed: Jan. 11, 2014

(65) Prior Publication Data

US 2014/0222109 A1 Aug. 7, 2014

Related U.S. Application Data

(60) Provisional application No. 61/761,707, filed on Feb. 7, 2013, provisional application No. 61/906,902, filed on Nov. 21, 2013.

(51) Int. Cl.
*A61N 1/00* (2006.01)
*A61N 1/37* (2006.01)
*A61N 1/372* (2006.01)
*A61N 1/375* (2006.01)

(52) U.S. Cl.
CPC .............. *A61N 1/3708* (2013.01); *A61N 1/375* (2013.01); *A61N 1/37211* (2013.01); *A61N 1/37217* (2013.01); *A61N 1/37276* (2013.01)

(58) Field of Classification Search
CPC ........... A61N 1/37211; A61N 1/37276; A61N 1/3727; A61N 1/378; A61N 1/3708; A61N 1/375
See application file for complete search history.

(56) References Cited

U.S. PATENT DOCUMENTS

| 6,076,016 | A | 6/2000 | Feierbach | |
| 6,456,887 | B1 * | 9/2002 | Dudding | A61N 1/37252 607/31 |
| 7,945,333 | B2 * | 5/2011 | Jacobson | A61N 1/3704 607/30 |
| 8,547,248 | B2 | 10/2013 | Zdeblick et al. | |
| 2004/0167587 | A1 * | 8/2004 | Thompson | A61N 1/37252 607/60 |
| 2008/0294062 | A1 | 11/2008 | Rapoport et al. | |

(Continued)

FOREIGN PATENT DOCUMENTS

WO 2008/016194 2/2008

OTHER PUBLICATIONS

Wegmueller, Marc Simon, "Intra-Body Communication for Biomedical Sensor Networks", 2007, Diss. ETH No. 17323, Switzerland.

(Continued)

*Primary Examiner* — Mallika D Fairchild
(74) *Attorney, Agent, or Firm* — ARC IP Law, PC; Joseph J. Mayo

(57) ABSTRACT

An implantable medical device including a data communication device that includes a device that alters an oscillatory electric field imposed on body tissue surrounding the implantable device. The device that alters an oscillatory electric field modulates an impedance of a conductive medium surrounding the implantable device when the implantable device is within an oscillatory electric field. The device that alters an oscillatory electric field includes a device that generates an oscillatory electric field that is phase-synchronized with an oscillatory electric field imposed on a conductive medium surrounding the implantable device.

12 Claims, 12 Drawing Sheets

(56) References Cited

U.S. PATENT DOCUMENTS

| | | | |
|---|---|---|---|
| 2009/0204170 A1* | 8/2009 | Hastings | A61N 1/0565 607/33 |
| 2009/0228071 A1 | 9/2009 | Bourget | |
| 2010/0125315 A1* | 5/2010 | Parramon | A61N 1/0551 607/59 |
| 2011/0125214 A1 | 5/2011 | Goetz et al. | |
| 2011/0196452 A1 | 8/2011 | Forsell | |
| 2011/0288615 A1 | 11/2011 | Armstrong et al. | |
| 2012/0004708 A1 | 1/2012 | Chen et al. | |
| 2012/0029323 A1 | 2/2012 | Zhao | |
| 2012/0101545 A1 | 4/2012 | Wahlstrand et al. | |

OTHER PUBLICATIONS

European Search Report issued for EP Application No. 14153810.8 dated May 9, 2014, 6 pages.

\* cited by examiner

IMPLANTABLE MEDICAL DEVICE, MEDICAL SYSTEM AND METHOD FOR DATA COMMUNICATION

This application claims the benefit of U.S. Provisional Patent Application 61/761,707, filed on 7 Feb. 2013, and U.S. Provisional Patent Application 61/906,902, filed on 21 Nov. 2013, the specifications of which are hereby incorporated herein by reference.

BACKGROUND OF THE INVENTION

1. Field of the Invention

At least one embodiment of the invention generally relates to implantable medical devices and data communication from implantable medical devices to an external device.

2. Description of the Related Art

Typically, implantable devices, in particular implantable medical devices, such as implantable therapy and/or monitoring devices including pacemakers, cardioverters and defibrillators or the like, may include data communication means to transmit data from the implantable medical device to an external device or vice versa. The data communication means, generally, may be used when the implantable medical device is implanted in the body of a mammal or when it is stored in a conductive package prior to the implantation.

A system for data communication with a medical device thus, generally, includes an implantable medical device and an external device such as a programmer or a communication device.

A typical implantable medical device comprises a battery, a monitoring and/or therapy control unit, in some cases additionally one or more therapy units such as stimulation units and a memory for storing control program and/or data sensed by the implantable medical device. If the implantable medical device is a pacemaker or an implantable cardioverter/defibrillator (ICD), generally, the therapy units comprise stimulation units for generating and delivering electric stimulation pulses to a patient's heart tissue (myocardium). Often, sensing units for sensing cardiac activity are provided. Sensing units, typically, may process electrical signals that represent electrical potentials that may be picked up via electrodes, e.g., in a heart.

Generally, in order to transmit data sensed by the implantable medical device to an external device, a telemetry unit may be provided. Typically the telemetry unit may allow a bidirectional data communication, that is, the telemetry unit may transmit and receive data wirelessly.

Limited battery capacity of an implantable medical device generally calls for energy-efficient data communication. An implantable medical device with limited battery power typically requires a low power communication scheme in order to program it and to download acquired data. With extremely low power communication, device longevity may be increased and longer communication sessions may be achieved.

Typical communication schemes or data communication by a telemetry unit may involve RF, magnetic, ultrasonic or galvanic communication. RF frequencies of ~400 or ~900 MHz or magnetic coupling in the 100s of kHz range typically require several mA of current to transmit and receive data. Such high current requirements are generally out of reach of devices with battery capacities of at most a few hundred mAh. Active transmission of galvanic pulses, generally, may also require several mA of current.

In addition, RF schemes typically require relatively large antennas and magnetic coupling requires large transmit and receive coils for communication. These transmission schemes, generally, also do not penetrate the body effectively and have ranges on the order of 5-10 cm. The space available in an implantable leadless pacer (iLP), for instance, typically would not allow such large coils or antennas. iLPs are generally designed to be placed within a heart chamber as opposite to conventional pacemakers, where the pacemaker itself is placed outside the heart and electrode leads extend from the pacemaker into the heart.

In view of the above, there is a need for a low-power communication scheme that does not employ RF or magnetic coupling.

BRIEF SUMMARY OF THE INVENTION

One or more embodiments of the invention are related to implantable medical devices and data communication from implantable medical devices to an external device.

Objectives of the invention according to at least one embodiment of the invention include providing an implantable medical device with a data communication method that may cause minimal battery drain from the medical device's battery. The data communication method, in at least one embodiment, may be used while the implantable medical device is sensing physiological signals. In one or more embodiments, an implantable medical device may be provided that comprises one or more data communication devices which include one or more devices that alter an oscillatory electric field imposed on a conductive medium surrounding the implantable medical device. The conductive medium, in embodiments of the invention, is either the body tissue when the implantable medical device is implanted in the body of a mammal or a conductive package in which the implantable medical device is stored prior to the implantation.

Embodiments of the invention include modulation of impedance surrounding the implantable medical device within an electric field to communicate between a small implantable medical device implanted in the heart or body or stored in a conductive package, and an external device such as a programmer or communication device. Alternatively, in at least one embodiments, the implantable medical device may generate a small electric field to facilitate this same communication. In one or more embodiments, the external device may use surface electrodes to impart an oscillatory electric field on the body or package that encompasses the implantable medical device, and a second set of electrodes that may sense the impedance change.

In at least one embodiment, the one or more devices that may alter an oscillatory electric field may modulate an impedance surrounding the implantable medical device when the implantable medical device is within a conductive medium within an oscillatory electric field. The external device, in at least one embodiment, may use surface electrodes to impart an oscillatory electric field that encompasses the implantable medical device. In embodiments of the invention, the oscillatory electric field may include an oscillation frequency in the range of 50 kHz to 1 MHz and preferably may include an oscillation frequency in the range of 400-700 kHz. The implantable medical device, in at least one embodiment, within the field, may alternate shorting and opening of an internal connection between two electrodes on its surface to change the impedance across the space of the implantable medical device. The change in impedance may be sensed by the external device as changes in either current or voltage of the imparted oscillatory field in the vicinity of the implantable medical device. In at least one embodiment, a lock-in amplifier may be used to average the small voltage or current change over several cycles of the injected field. The changes in voltage or current, in embodiments of the invention, may be modulated to form a communication scheme to transmit data.

In embodiments of the invention, the one or more devices that may alter an oscillatory electric field may include one or more devices that may generate an oscillatory electric field that is phase-synchronized with an oscillatory electric field imposed on the implantable medical device when the implantable medical device is surrounded by a conductive medium. The external device, in at least one embodiment, may use surface electrodes to impart an oscillatory electric field that encompasses the implantable medical device. The implantable medical device, in embodiments of the invention, then may monitor this field and may generate a small electric field which is phase-synchronized with the external devices field in order to facilitate reception of this small field by the external device using a lock-in amplifier. The small changes in the electric field, in one or more embodiments, may be sensed by the external device as changes in voltage or current of field surrounding the implantable medical device. The changes in voltage or current, in at least one embodiment, may be demodulated to form a communications scheme from the implantable medical device to the external device. Synchronization with the external field may allow the implantable device to generate a much smaller electric field than would otherwise be required to communicate with the external device.

In at least one embodiment, the implantable medical device may generate a small oscillatory field at a predetermined frequency between its electrodes. The external device, in one or more embodiments, may sense this frequency and phase-locks to it in order to facilitate reception of the small field using a lock-in amplifier. The oscillatory field generated by the implantable medical device may be on the order of 1 mV-50 mV and preferably around 30 mV. The changes in oscillatory may be demodulated to form a communications scheme from the implantable medical device to the external device. In embodiments of the invention, synchronization with the external field may allow the implantable device to generate a much smaller electric field than would otherwise be required to communicate with the external device. By generating an oscillatory field and sensing the field using a lock-in amplifier, in at least one embodiment, communication may be extended to occur between two implantable medical devices.

Because very little power is required for data transmission, in embodiments of the invention, an implantable medical device with limited battery supply may have the ability to transmit increased amount of data while using very little power. Data transmission may be achieved by modulating an electric field surrounding the device and read by the receiver as changing voltage or current in at least one embodiment. Continuous medium rate data transmission may be achieved while using very little battery power.

Preferably, in one or more embodiments, the implantable medical device may include a switch, such as a FET, relay, BJT, or similar switching device, and at least two electrodes that may be connected to the switch such that the at least two electrodes may be electrically connected or disconnected, respectively, by the switch. In one or more embodiments, the at least two electrodes may cause a change of impedance when the implantable medical device is surrounded by a conductive medium, such as body tissue or a conductive package, and the electrodes are connected or disconnected, respectively, using the switch, e.g., a switch or in particular a low impedance solid state switch.

In one or more embodiments, one electrode, such as a tip electrode, may be arranged at the tip of the implantable medical device. Another electrode, a ring electrode, may be arranged on or around the surface of the implantable medical device. In at least one embodiment, the tip and ring electrodes may be used to pace a heart by inducing electrical cardiac activity (pacing), to sense the electrical activity of a heart (sensing), and/or to alter the local electric field for data communication to transmit data to an external device (transmitting). A preferred frequency for data communication, in embodiments of the invention, may be 4-8 kHz, but a suitable range may also be 1-20 kHz. The implantable medical device, in one or more embodiments, may also include more electrodes, e.g., a pair of electrodes for each of the tasks (pacing, sensing, and transmitting) of the implantable medical device.

By way of one or more embodiments, the at least one switch may be connected to a switch control that may sense an oscillatory electric field imposed on the implantable medical device. Thus, in at least one embodiments, it is possible to synchronize connecting and disconnecting of the at least two implantable electrodes with the oscillatory electric field imposed on conductive medium surrounding or encompassing the implantable medical device.

To implement such synchronizing, in embodiments of the invention, the switch control may include a phase-locked loop (PLL) and a frequency divider, wherein the phase-locked loop may lock in a frequency of an oscillatory electric field imposed on body tissue surrounding the implantable medical device when the implantable medical device is in its implanted state. The PLL is desirable when fast transmitting speeds are required, thus reducing the number of cycles of the external oscillatory field when the switch is active in order to decode the modulated carrier signal at the external device. In one or more embodiments, the frequency divider may be connected to the phase-locked loop and may divide a frequency signal outputted by the phase-locked loop. Thus, in at least one embodiments, the implantable medical device may generate a code that may represent data to be transmitted from the implantable medical device to an external device, wherein the clock for such code may be a fraction of the frequency of the oscillatory electric field imposed on the body tissue surrounding the implantable medical device. The clock frequency, in embodiments of the invention, may be in a range of 0.1 to 50 kHz, such as a range of 1 to 20 kHz, or in a range of 4 to 10 kHz, or at a frequency of 8 kHz.

According to at least one embodiment, the switch control may be connected to the at least two electrodes and may sense an oscillatory electric field imposed on the at least two electrodes. The switch control, in embodiments of the invention, may include a band-pass filter, wherein the band-pass filter may filter a signal fed to the phase-locked loop.

In at least one embodiment of the invention, a PLL may not be required and the switching of the electrodes may not be synchronized to the external oscillating field. Because the external oscillating field may be at a much higher frequency than the frequency of switching within the device, for example approximately 100:1, the lock-in amplifier may able to adequately amplify the received signal according to embodiments of the invention.

In at least one embodiment, the device that alters an oscillatory electric field may include a field generating device that generates an oscillatory electric field that may be phase-synchronized with an oscillatory electric field imposed on a conductive medium surrounding the implantable medical device. An implantable medical device according to one or more embodiments may further include a field generation controller that may be operatively connected to the field generating device and may control the field generating device in response to an oscillatory electric field imposed on a conductive medium surrounding the implantable medical device.

The implantable medical device, in at least one embodiment, may include at least one sensor that may sense electrograms. Preferably, in one or more embodiments, the implantable medical device may allow simultaneous communication between the implantable medical device and an external device and sensing of electrograms.

The implantable medical device, in at least one embodiment, may include pace/sense circuitry comprising a DC blocking capacitor and input amplifiers for impedance measurements and capture control. Input amplifiers for impedance measurements and capture control, in one or more embodiments, may become saturated after pacing pulses are delivered to a heart. The excess energy may then be deposited on the DC blocking capacitor and removed by shorting the DC blocking capacitor across the electrodes, which may cause the input amplifier to saturate. In at least one embodiment, the electrodes of the implanted medical device may create a slight half-cell potential between the metal of the electrodes and the blood electrolyte. This potential may be a DC voltage that may be filtered by the input amplifier and may not affect sensing. If the electrodes are shorted together, in embodiments of the invention, as may occur during modulation of the oscillatory field, there may be an instantaneous change in the potential that requires several milliseconds to restabilize. The time constant may be dependent on the tissue impedance. The instantaneous change in potential, in embodiments of the invention, may cause the input amplifier to saturate, during which time no electrograms may be sensed.

In at least one embodiment of the invention, a device that maintains any DC potential and other low frequency signals across the device electrodes, such as a capacitor, may be placed in series with the at least one switch, or in series with the at least one switch and between the two electrodes that may be connected and/or disconnected by the at least one switch that may cause a change of impedance. In embodiments of the invention, the capacitor may serve to maintain a DC voltage on the electrodes when they are connected by the at least one switch. By maintaining the DC voltage on the electrodes, in at least one embodiment, the implantable medical device may sense electrical cardiac activity and simultaneously communicate with an external device. It is thus not required to limit the data communication to "safe" windows when sensing may not be required.

Preferably, in one or more embodiments, the switch may cause low charge injection and may be of low impedance. Charge injection by the switch may cause slight noise on the electrogram sensing. In one embodiment there is a trade-off between charge injection and switch impedance. If charge injection by the switch is high, in at least one embodiment, the charge may be deposited on the capacitor and the electrodes and may cause switching artifacts. An electrogram may nonetheless be acquired but high frequency noise may be present. Switch impedance may affect the amplitude of the reflected signal to the external device. The higher the impedance the lower the reflected signal. In one or more embodiments, the capacitor may have low impedance to high frequency, e.g., 1 Ohm and high impedance to DC and low frequency, preferably larger than 2500 Ohms. Shorting together the electrodes by the switch may short a high frequency carrier signal through the capacitor and may alters the local high frequency electric field, in embodiments of the invention, which may effect communication. Low frequency physiologic signal and DC offset voltage on the electrodes may not be affected and maintained by the capacitor. Additionally, in at least one embodiment, an additional resistor may be placed in parallel with a switch of the at least one switch and in series with the capacitor, in order to maintain DC voltage on the capacitor when communication may not be active.

Embodiments of the invention with an electrogram amplifier front-end may include an electrogram amplifier, an input resistor, and a filter resistor in combination with a filter capacitor, which may form a low-pass filter at the electrogram amplifier front-end. When the switch is closed, in at least one embodiment, the input resistor may be shorted to low impedance and most of the input voltage may fall across the filter capacitor. The filter capacitor, in embodiments of the invention, may also act to maintain the DC potential on the electrodes since it may be continually charged by the filter resistor bypassing the at least one switch. When the switch is open, in one or more embodiments, the filter resistor and filter capacitor may act as a low-pass filter, e.g., with 39 kOhms and 33 nF the low-pass filter may have a cutoff frequency of about 124 Hz. The filter may be used to prevent high frequency noise from entering the amplifier. When the switch is closed, in at least one embodiment, the filter cutoff frequency may be shifted to a higher frequency in dependence on the switch impedance, e.g., preferably slightly below the carrier frequency, while electrogram acquisition is maintained. The high frequency carrier signal used for conductive intra-body communications/impedance-communication may be shunted through the capacitor to the other electrode. Shunting of the high frequency, in embodiments of the invention, may alter the local electric field around the implantable medical device allowing communication.

At least on embodiment of the invention may include a data communication system including an implantable medical device as described above and an external device that may include or may be connected to at least two surface electrodes. The external device, in at least one embodiment, may include an external field generator, such as a current or voltage source, that may generate an oscillatory electric field to be imposed on a body or other conductive medium, such as a package via the at least two surface electrodes. The external device, in embodiments of the invention, may include at least one sensor configured to sense alterations of body or package impedance and/or an oscillatory electric field that may be generated by the implantable medical device.

The external device, in at least one embodiment, may include a lock-in amplifier, an AM demodulator that may demodulate amplitude-modulated signals and an analog-to-digital converter, wherein the analog-to-digital converter may be operatively connected to the AM demodulator and the lock-in amplifier, and wherein the analog-to-digital converter may output a signal that may represent a signal transmitted by the implantable medical device. Embodiments of the invention may include four electrodes, two for injecting the field and two to receive the modulated signal from the implantable medical device.

In at least one embodiment, the external device may receive alterations of impedance that may be modulated to encode data in a binary phase shift key method. The AM demodulated signal, in at least one embodiment, may be encoded in such a manner that there are no long periods in which the implantable medical device switch is in any single position, either on or off. One example of such an encoding scheme may be to encode a logical '1' as modulating the switch closed-open-closed-open and a logical '0' as modulating the switch open-closed-open-closed. In this manner, in at least one embodiment, the switch may be either closed or open twice as long when transitioning from a '0' to '1' or '1' to '0', respectively. The fundamental frequency of switching is thus maintained and narrower band-pass filters may be used in the lock-in amplifier. This in turn may increase signal-to-noise ration of the received communication from the implantable medical device.

In at least one embodiment, the external device may use two lock-in demodulators phase shifted by 90 degrees. By demodulating the received signal at, for example 0 degrees and 90 degrees, in one or more embodiments, the external device may maintain a high signal-to-noise ratio by combining the two signals. Phase information may also be decoded based on the difference in amplitude of the two output signals. Phase information may be used to implant more advanced modulating schemes in the implantable medical device. For example, in at least one embodiment, the oscillatory field that may be generated by the implantable medical device may be phase shifted such that the output at the external device is either positive or negative, depending on the phase output. As such, a continuous oscillatory field may be realized where phase shifting segments encodes data in the communication. Further, in embodiments of the invention, phase discrimination may allow determination of the implantable device with respect to the receiving electrodes.

In at least one embodiment of the invention, only two electrodes may be used to both impart the oscillatory field on a body or other conductive medium such as a package, and to receive the modulated signal from the implantable medical device. In this configuration, in one or more embodiments, a Wheatstone bridge may be used such that the imparted signal may be between the surface electrodes and the received signal may be between one surface electrode and an internal connection. Using two surface electrodes for the external device may reduce external components and may simplify operation.

In at least one embodiment, the implantable device, i.e. implantable medical device, may include a hermetically sealed housing. The hermetically sealed implantable device or implantable medical device with a hermetically sealed housing may be a medical therapy and/or monitoring device, according to embodiments of the invention.

At least one embodiment may include a method of communicating data from an implantable medical device to an external device, wherein the method may include:
 imposing an oscillatory electric field on a conductive medium encompassing an implantable medical device,
 altering the oscillatory electric field using the implantable medical device by inducing an alternating change of impedance using the implantable medical device or by generating a small oscillatory electric field using the implantable medical device, and
 sensing the change of impedance or the small oscillatory electric field generated by the implantable medical device, respectively, using an external device having or being connected to at least two surface electrodes.

In one or more embodiments, the method may include the step of sensing the imposed oscillatory electric field using the implantable medical device after the step of imposing an oscillatory electric field on a conductive medium encompassing an implantable medical device. In this case the implantable medical device may communicate only if an oscillatory electric field is detected.

Preferably, in at least one embodiment, the step of altering the oscillatory electric field using the implantable medical device may be performed using at least two electrodes that may be operatively connected or be part of the implantable medical device, and at least one switch operatively connected to the at least two electrodes, wherein the at least one switch may connect and disconnect the at least two electrodes in an alternating manner according to a code-representing data to be transmitted from the implantable medical device to the external device. In one or more embodiments, the alternating connecting and disconnecting may cause a detectable change of impedance for the imposed oscillatory electric field. In at least one embodiment, the at least one switch may include a high impedance at low frequency and low impedance at high frequency and may be in series with a capacitor or other means to maintain a DC voltage on said electrodes.

The method of data communication, in one or more embodiments, may include data communication from an external device to an implantable device. In at least one embodiment, the method may include the step of modulating the oscillatory electric field using the external device.

BRIEF DESCRIPTION OF THE DRAWINGS

The above and other aspects, features and advantages of at least one embodiment of the invention will be more apparent from the following more particular description thereof, presented in conjunction with the following drawings wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
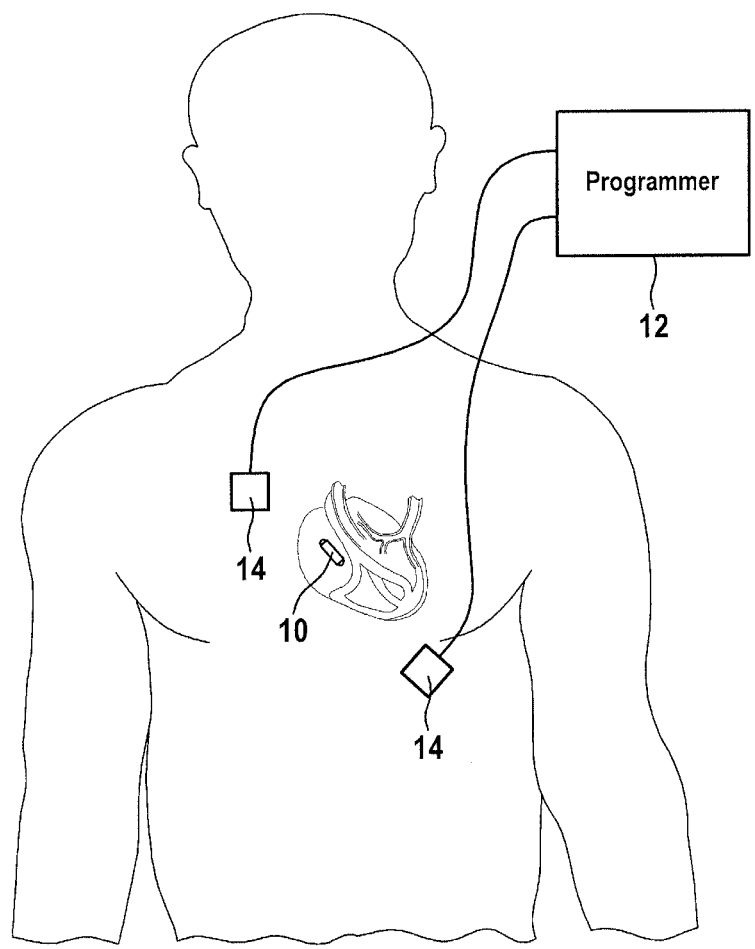
FIG. 1 shows a representation of a communication system, including an implantable medical device in its implanted state and an external device, according to one or more embodiments of the invention.

FIG. 1 shows a representation of a communication system, comprising including an implantable medical device in its implanted state and an external device, according to one or more embodiments of the invention. As shown in FIG. 1, one or more embodiments of the invention, may utilize an implanted pacemaker such as an implantable medical device 10, a programmer or communication device such as external device 12, and cutaneous electrodes 14 that may be placed on either side of the heart. In at least one embodiment, the external device 12 may induce an oscillating electric field between the electrodes between 50 kHz to 1 MHz, preferably between 50 to 100 kHz, at a voltage or current. The medical device implanted in the heart, in embodiments of the invention, may be located between the two surface electrodes 14.

Figure 2:
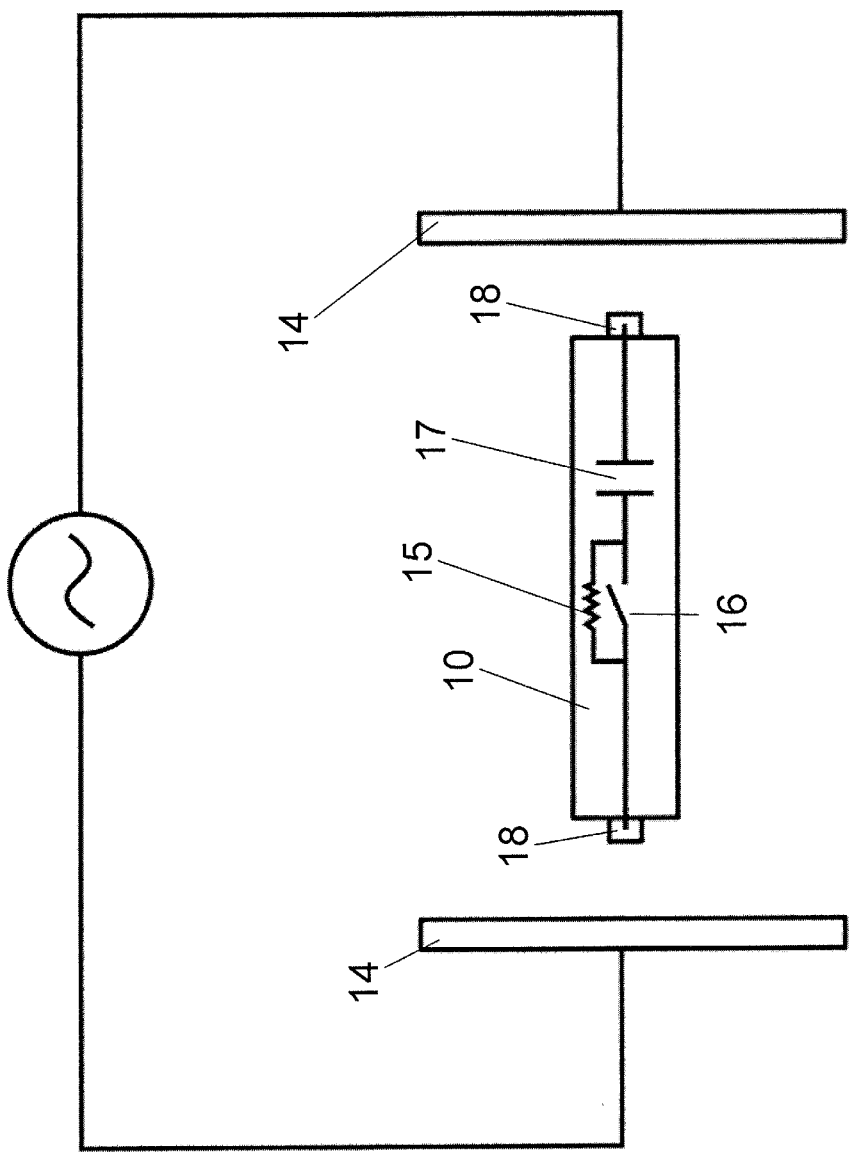
FIG. 2 shows a more abstract representation of the system depicted in FIG. 1, according to one or more embodiments of the invention.

FIG. 2 shows a more abstract representation of the system depicted in FIG. 1, according to one or more embodiments of the invention.

Figure 3:
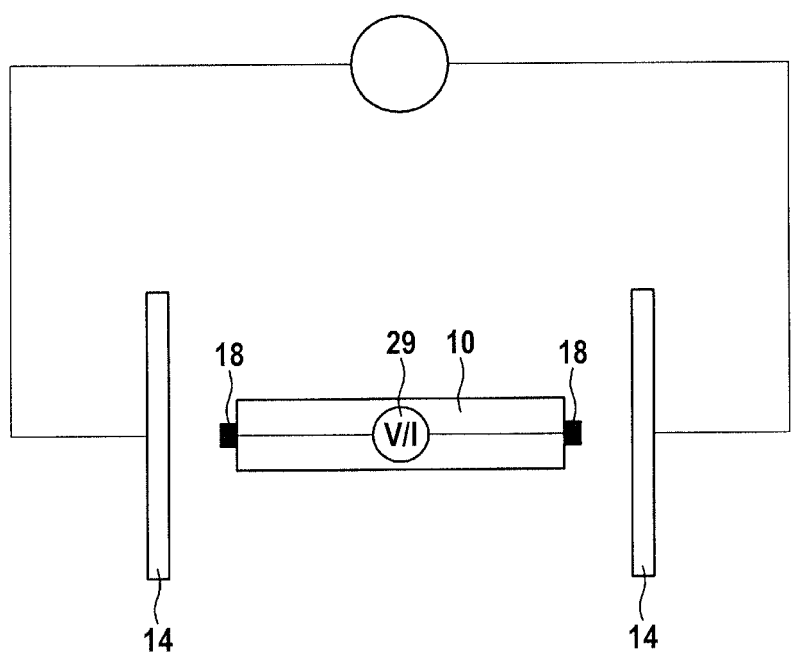
FIG. 3 shows an alternative embodiment of the system depicted in FIG. 1, according to one or more embodiments of the invention.

FIG. 3 shows an alternative embodiment of the system depicted in FIG. 1, according to one or more embodiments of the invention.

Figure 6:
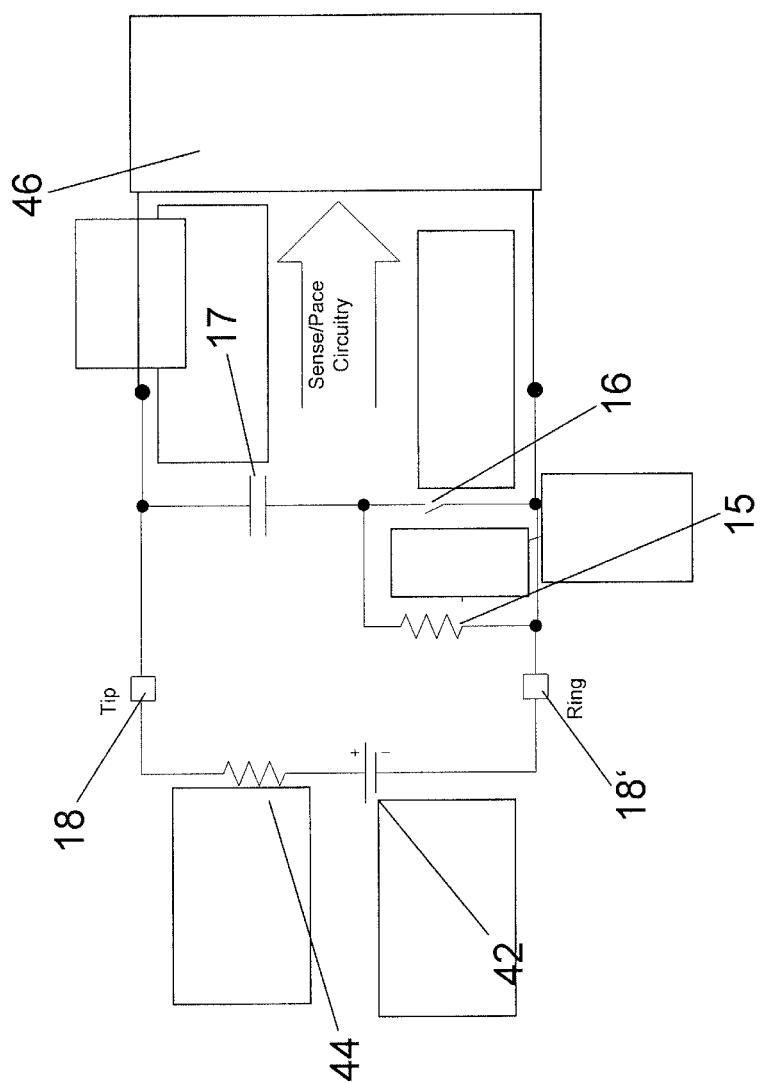
FIG. 6 shows a representation of a configuration of a passive Z-COMM switch, according to one or more embodiments of the invention.
Figure 7:
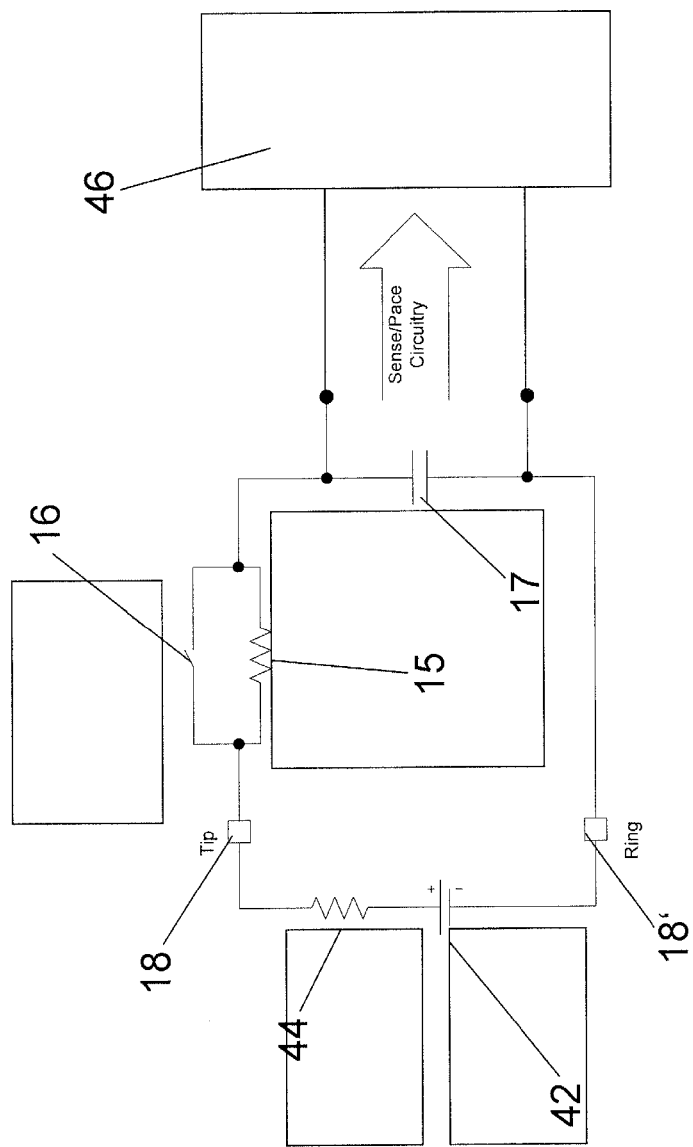
FIG. 7 shows a representation of a low-pass filter implementation of a switch circuit, according to one or more embodiments of the invention.

It should be noted that an implantable medical device 10 such as an implantable heart stimulator, according to embodiments of the invention, may include a battery, a monitoring and/or therapy control unit, one or more therapy units such as stimulation (pacing) units, sensing units or the like, pace/sense circuitry 46 as shown in FIG. 6 and FIG. 7, and a memory that may store control program and/or data sensed by the implantable medical device. If the implantable medical device 10 is a pacemaker or an implantable cardioverter/defibrillator (ICD), in at least one embodiment, the therapy units may include stimulation units that may generate and deliver electric stimulation pulses to a patient's heart tissue (myocardium). Stimulation units may be connected to stimulation electrode leads in embodiments of the invention.

Figure 4:
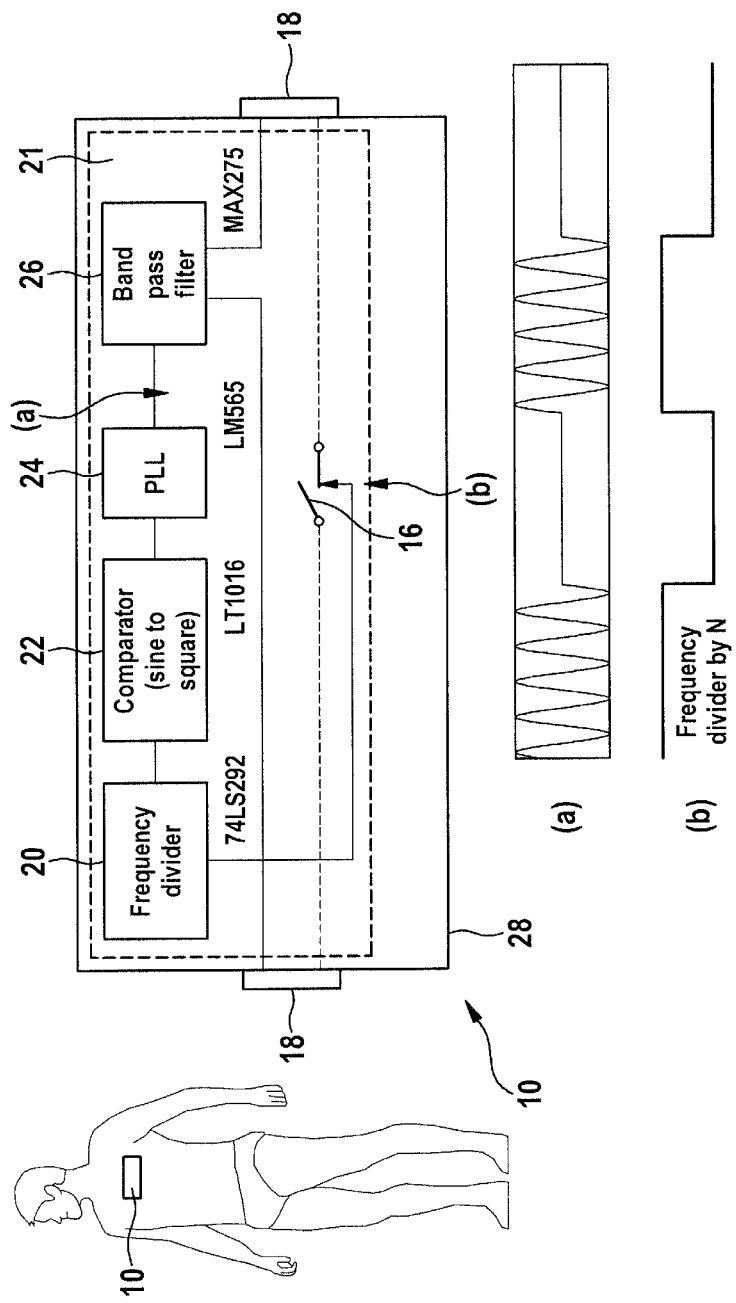
FIG. 4 shows a more detailed representation of another alternative embodiment of an implantable device according to one or more embodiments of the invention.
Figure 5:
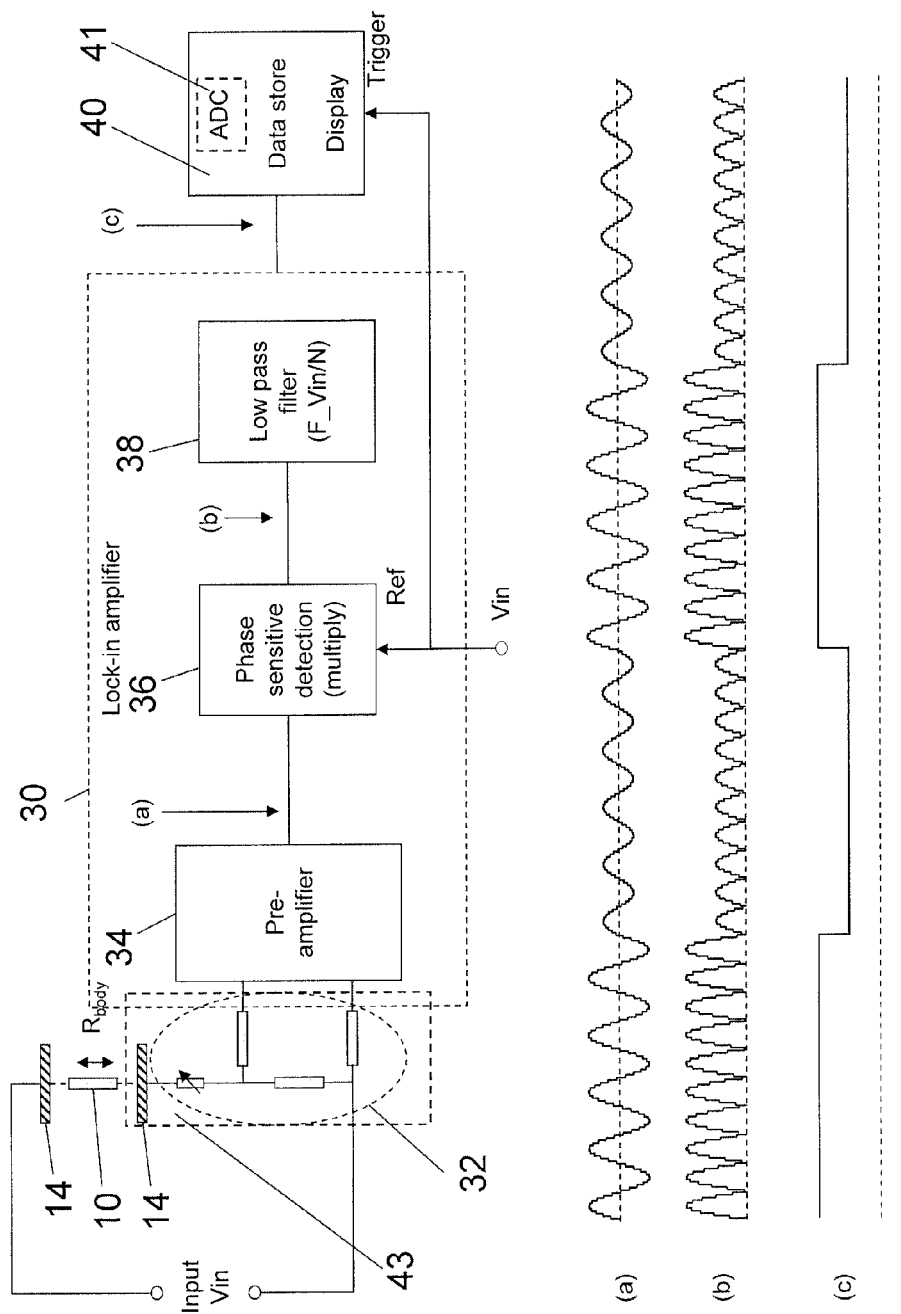
FIG. 5 shows a more detailed representation of an external device according to one or more embodiments of the invention.

According to one or more embodiments, in order to transmit data sensed by the implantable medical device 10 to an external device 12, a telemetry unit may be provided. In at least one embodiment, the telemetry unit may allow a bidirectional data communication, that is, the telemetry unit may transmit and receive data wirelessly. FIGS. 4 and 5 illustrate details of internal and external therapy units, respectively, according to one or more embodiments of the invention.

FIG. 4 shows a more detailed representation of another alternative embodiment of an implantable device according to one or more embodiments of the invention.

Referring to FIG. 4, the implantable medical device 10 may include two (implantable) electrodes 18 that may contact body tissue surrounding the implantable medical device 10 in its implanted state. In embodiments of the invention, the at least one switch may be at least one simple switch 16 that may connect or disconnect, respectively, the two electrodes 18 in order to establish or interrupt an electrical connection between the electrodes 18. The electrical connection across the at least one switch 16 may be of low ohmic resistance. In at least one embodiment, the at least two electrodes 18 of the implantable medical device 10 may be arranged on the external surface of a hermetically sealed housing 28 encapsulating the implantable medical device 10. According to at least one embodiment, parts of the housing 28 itself may form the at least two electrodes 18. The electrodes 18, in embodiments of the invention, may also be formed by a tip electrode 18 located at a tip of the implantable medical device 10 and a ring electrode 18' located on the circumference of the implanted medical device 10 (not shown).

If the implantable medical device is connected to leads carrying electrodes in contact with body tissue, in at least one embodiment, any two of these electrodes including the conductive housing may be used as electrodes 18.

In order to control the at least one switch 16, by way of one or more embodiments, the implantable medical device 10 may include a frequency divider 20 that may be connected to a sine-to-square converting comparator 22 that in turn may be connected to a phase-locked loop (PLL) 24. Phase-locked loop 24, in embodiments of the invention, may be connected to the electrodes 18 via band-pass filter 26. Phase-locked loop 24 and frequency divider 20 may be part of a switch control of implantable medical device 10.

In at least one embodiment, the field induced between the surface electrodes 14 may be sensed by the implantable medical device 10. The implantable medical device 10 may lock in the frequency of the electric field using the phase-locked loop 24. Once the implantable medical device 10 may be locked on to the frequency of the external device's induced field, in at least one embodiment, it may activate the at least one switch 16 between the two electrodes 18 that may be in the field (as shown in FIGS. 2 and 4 for example) in synch with the frequency of the electric field.

In more detail, according to one or more embodiments, the implantable medical device 10 may receive the imposed oscillatory electric signal as input signal that may be detected via the electrode 18 or across a resistor. Thus, in at least one embodiment, the implantable medical device may include an input sine signal that may be detected as an alternating voltage across electrodes 18 or across a resistor. This input sine signal may be band-pass filtered by band-pass filter 26 in embodiments of the invention. A representation of that band-pass filtered signal is shown in diagram (a) of FIG. 4.

By way of one or more embodiments, the band-pass filtered input sine signal may be fed to the phase-locked loop (PLL) 24 that may lock in the frequency of the input sine signal. Phase-locked loop 24, in at least one embodiment, may output a synchronized sine signal to a comparator 22 that may convert the sine signal shown in diagram (a) of FIG. 4 to a square signal as shown in diagram (b) of FIG. 4. The square signal generated, in embodiments of the invention, may be fed to frequency divider 20 that may generate a clock signal for switching the at least one switch 16. The clock signal generated, in one or more embodiments, may include a frequency corresponding to a fraction of the frequency of the oscillatory electric field wherein the fraction may be determined by a frequency division factor applied by frequency divider 20. The clock signal frequency, in embodiments of the invention, may be in a range of 0.1 to 50 kHz, such as a range of 1 to 20 kHz, in a range of 4 to 10 kHz, such as a clock signal frequency of 8 kHz.

The actual switching of the at least one switch 16, in at least one embodiment, may depend on data that may be transmitted from the implantable medical device 10 to the external device 12. The data to be transmitted may be coded and the code may determine the actual sequence of switching of the at least one switch 16.

In one or more embodiments, frequency divider 20 may be a flip-flop counter. In embodiments of the invention, the at least one switch 16 may have a small on-resistance. The latter aspect may lead to change of impedance, depending on whether the at least one switch 16 is opened or closed.

In at least one embodiment, such change of impedance may be sensed by external device 12.

In one or more embodiments, data transmission from the implantable medical device 10 to the external device 12 thus may be summarized as follows:

Apply signal (oscillatory electric field), propagate in body, switch on/off of the at least one switch 16 in implantable device 10, impedance change of body, detect change by external device 12.

By way of one or more embodiments, the switch control of the implantable medical device 10 may receive an input sine signal by detecting a voltage across electrodes 18 or across a resistor. The switch control of the implantable medical device 10 according to at least one embodiment, may include band-pass filter 26, phase-locked loop 24 to lock in the frequency of the input sine signal, comparator 22 to convert the sine signal to a square signal, a flip-flop counter that may act as frequency divider 20, that may control the at least one switch 16. In embodiments of the invention, the at least one switch 16 may include a small on-resistance.

In at least one embodiment, the impedance changes caused by the implantable medical device 10 may be detected by the external device 12.

FIG. 5 shows a more detailed representation of an external device according to one or more embodiments of the invention.

As shown in FIG. 5, in at least one embodiment, the external device 12 may include a lock-in amplifier 30 that may generate an output signal (such as the shown in diagram (c) of FIG. 5) that represents the signal transmitted by implantable medical device 10 by way of impedance changes. In one or more embodiments, lock-in amplifier 30 may use the signal imposed on a body via the surface electrodes 14 as a reference signal. For this purpose, in embodiments of the invention, a network of resistors 32 may be provided that may cause a voltage drop representing the signal (the oscillatory electric field) imposed on a body via surface electrodes 14.

This signal may be amplified by pre-amplifier 34 of lock-in amplifier 30 according to embodiments of the invention.

By way of one or more embodiments, the amplified signal sensed via sensing means 43, i.e. surface electrodes 14 and the resistor network 32 may be fed to an AM demodulator that may include a phase-sensitive detector 36 and may be further fed to a low-pass filter 38, as depicted in FIG. 5. The amplified input signal sensed via surface electrodes 14 and the resistor network 32 is represented as signal (a) in FIG. 5 (*a*). The output signal of the phase-sensitive detector 36 is depicted as signal (b) in FIG. 5 (*b*). The low-pass filtered output signal of lock-in amplifier 30 is depicted in FIG. 5 (*c*) as signal (c). Signal (c), in at least one embodiment, may correspond to the signal generated by implantable medical device 10 and thus may represent data to be transmitted from implantable medical device 10 to external device 12. In embodiments of the invention, this signal may be analog-to-digital converted and stored. Block 40 in FIG. 5 represents an analog-to-digital converter (ADC) 41, a memory for data storage and a display of external device 12.

In at least one embodiment, for the detection of impedance changes of the body caused by the implantable medical device 10, the external device 12 may include a lock-in amplifier 30 that may use the input as reference signal, including an AM demodulator which in turn may include a precision rectifier and a low-pass filter 38. The low-pass filtered signal may be fed to an analog-to-digital converter 41.

In at least one embodiment, the communication from implantable medical device 10 to external device 12 may be understood as follows.

As the implantable medical device 10 alternatively shorts and opens the connection between the electrodes 18, in one or more embodiments, the impedance between the external device electrodes 14 may be slightly changed or modulated. The external device 12 may sense the change in impedance by measuring how much voltage or current is imparted on the electrodes 14 to create the oscillator electric field between the external device electrodes 14.

In at least one embodiment, the external device 12 may sense the change in impedance using a lock-in amplifier 30 that may be synchronized to the electric field frequency and phase. As the implantable medical device 10 modulates the impedance between the external device electrodes 14, in at least one embodiment, the external device 12 may integrate the changing current or voltage. The integration may allow a very small change in sourced voltage or current to be detected using amplitude modulation.

Figure 9:
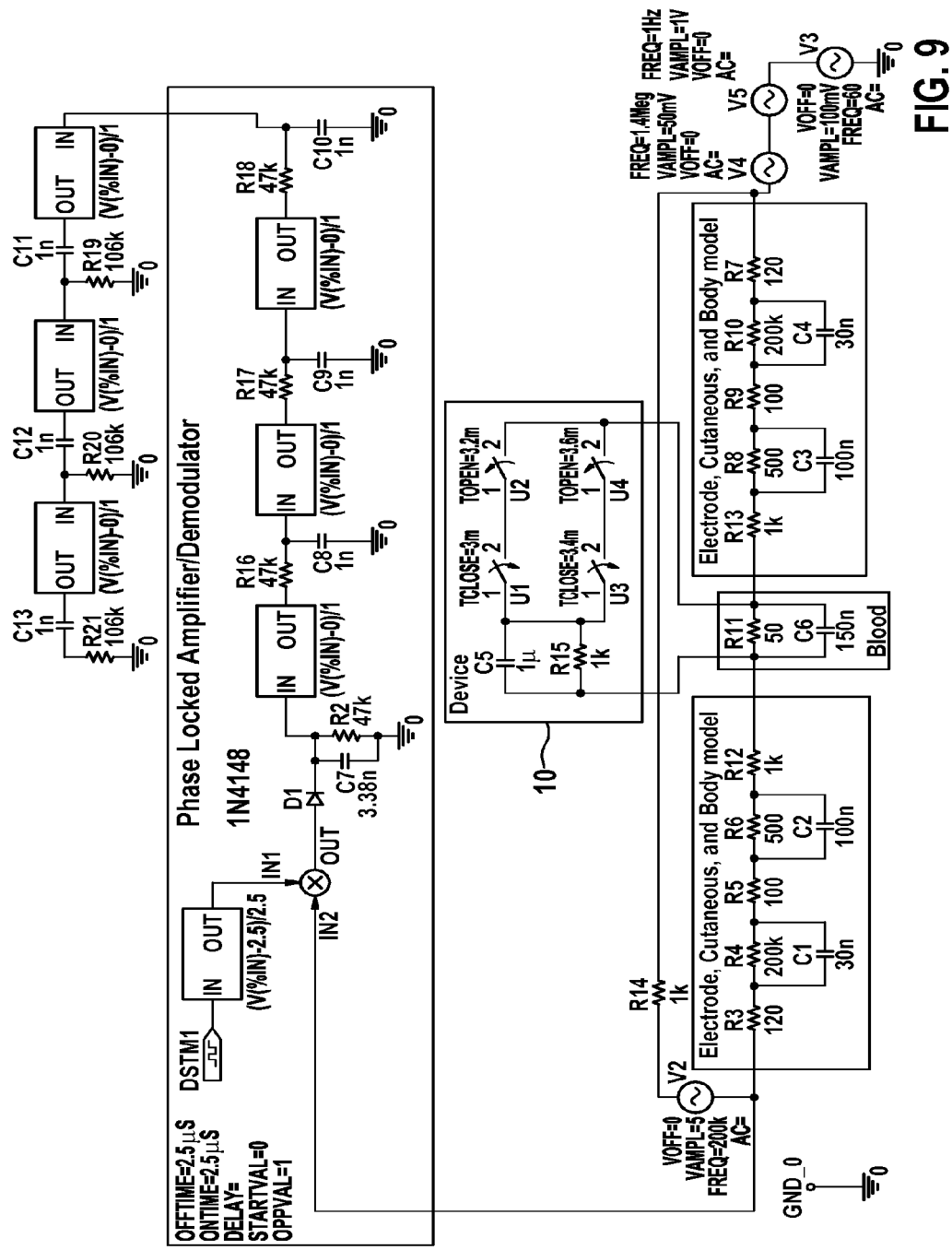
FIG. 9 shows a circuit diagram for a simulation scenario for simulating impedance change based data communication, according to one or more embodiments of the invention.
Figure 10:
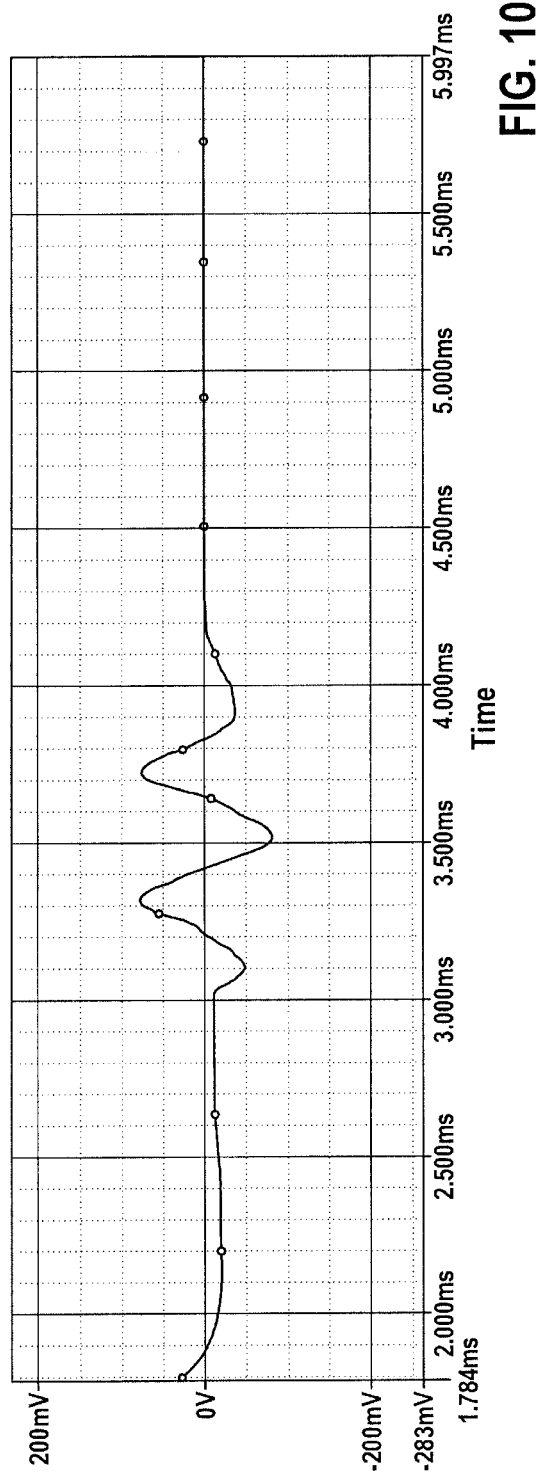
FIG. 10 shows a plot illustrating a simulation result achieved by using the diagram depicted in FIG. 9, according to one or more embodiments of the invention.

In one or more embodiments, communication may occur at approximately $1/10$ to $1/200$th of the modulation frequency of the oscillatory electric field. This allows for ~10-100 cycles of the electric field to be integrated to determine the imparted current or voltage. A model and simulation of the embodiment is shown in FIGS. 9 and 10 as will be discussed below.

In at least one embodiment, a small electric field may be generated by the implanted device 10 in place of passive resistance changes. In embodiments of the invention, the implantable medical device 10 may refer to circuitry that may be located between the two surface electrodes 14 of the external device 12. The surface electrodes 14 of the external device 12, in at least one embodiment, may impart an oscillatory electric field on the body that encompasses the implantable medical device 10. In one or more embodiments, the implantable medical device 10 may monitor this field and a field generating device 29 may generate a small electric field which may be phase-synchronized with the field of the external device 12 imposed on body tissue surrounding the implantable medical device 10 in order to facilitate reception of this small field by the external device 12 using a lock-in amplifier 30 (as shown in FIG. 5 for example). The implantable medical device 10 according to one or more embodiments may include a field generation controller that may be operatively connected to the field generating device 29 and may control the field generating device 29 in response to an oscillatory electric field imposed on a conductive medium surrounding the implantable medical device 10 when the implantable medical device 10 is in its implanted state or in a package. The small changes in the electric field may be sensed by the external device 12 as changes in voltage or current. The changes in voltage or current, in embodiments of the invention, may be demodulated to form a communications scheme from the implantable medical device 10 to the external device 12.

In at least one embodiment, the implanted device 10 may switch its impedance or small electric field at every other crest of the external device's applied electric field for ~10-100 cycles, called a chirp, in order to represent a mark of the communications scheme.

In one or more embodiments, a communication from external device 12 to implantable medical device 10 may be done as follows:

The imposed oscillatory electric field may include a fundamental frequency that the implantable medical device 10 uses to lock onto. The fundamental frequency may also be used as a carrier frequency to send modulated data to the implantable medical device 10. The external device 12 may modulate data, in at least one embodiment, using frequency modulation or amplitude modulation, on top of the carrier imparted electric field. In embodiments of the invention, the implantable medical device 10 may decode the modulated data sensed through the electrodes 18.

Embodiments of the invention may not require the implanted medical device 10 to actively transmit data using its own power in the case of impedance modulation embodiment. In embodiments of the invention, implanted medical device 10 may modulate a field imparted on it by an external device 12. In embodiments of the invention where the implantable medical device 10 may emit a low amplitude electric field, the phase-locked property that it maintains may allow for lower amplitude to be used for transmission to the external device 12 than if simple band-limited transmission schemes were used. In embodiments of the invention, the resulting drain on the implantable medical device's battery may be extremely small. Because of the small power consumption, it may be possible to transmit more data to the external device 12.

Saturation of input amplifiers is a problem for impedance measurements and capture control. This problem is solved as follows. After pacing pulses are delivered to a heart by the implantable medical device 10 the excess energy deposited on a DC blocking capacitor of the pace/sense circuitry 46 of the implantable medical device 10 must be removed. The DC blocking capacitor is shorted across the electrodes 18 to remove the excess voltage, which causes the input amplifier to saturate and which prevents sensing with the implantable medical device 10.

FIGS. 6 and 7 present embodiments of an implantable medical device 10 that allows communication with the external device 12 while sensing.

Specifically, FIG. 6 shows a representation of a configuration of a passive Z-COMM switch, according to one or more embodiments of the invention, and FIG. 7 shows a representation of a low-pass filter implementation of a switch circuit, according to one or more embodiments of the invention.

Conductive intra-body communication, in one or more embodiments, may use at least one switch 16 across a tip electrode 18 and a ring electrode 18' of an implantable medical device 10 to alter the local electrical field to transmit data to the external device 12. In at least one embodiment, the switching may cause large transient voltages to appear at the input amplifiers in a sense/pace circuitry 46 of the implantable medical device 10. The transient voltage may appear because of DC offsets at the device electrodes due to electrode electrolyte interface. The large transient voltage, in embodiments of the invention, may prevent sensing for several milliseconds thereby preventing sensing while communication with the external device 12 is ongoing. In at least one embodiment, electrically connecting a capacitor 17 in series with the data transmission switch 15 may allow maintenance the offset voltage and thereby reduction of the transient voltage produced by switching, such that sensing may be maintained.

FIG. 6 shows an electric circuit diagram of a part of an embodiment of an implantable medical device 10 in an implanted state with a conductive intra body communication at least one switch 16, a tip electrode 18 and a ring electrode 18' (sense/pace circuitry 46 part is not shown in detail and represented by a block 46 connected via connection points).

In at least one embodiment, an electrical double layer 42 (Helmholtz layer) may form on the surface of the ring 18' and tip electrodes 18 due to electrolytes that may be present in the blood interacting with the electrical potential at the electrodes 18 and 18'. The electrical double layer 42, in embodiments of the invention, may lead to a slight half-cell potential, which is represented as a DC voltage source for the implantable medical device 10 in the electric circuit diagram.

In one or more embodiments, a capacitor 17 may be electrically connected in series to the at least one switch 16 to maintain the DC voltage on the electrodes 18, when the at least one switch 16 is closed. When the at least one switch 16 shorts the electrodes 18 together, according to embodiments of the invention, a high frequency carrier signal may be shorted through the capacitor 17, and the local electric field may be altered due to an instantaneous change in the electrical potential dependent on the tissue impedance, which effects communication. The DC offset voltage on the electrodes 18, in embodiments of the invention, may not be affected and maintained by the capacitor 17 if the capacitor 17 has low impedance to high frequency, e.g., 1 Ohm and high impedance to DC and low frequency, preferably larger than 2500 Ohms.

An additional resistor 15, in at least one embodiment, may be electrically connected in parallel with the switch 16 to maintain DC voltage on the capacitor 17 when communication is not active. In embodiments of the invention, the additional resistor 15 is optional. An impedance 44 electrically, in at least one embodiment, may connect the electrical double layer 42 with the tip electrode 18 and may close the part of the electrical circuit of the implantable medical device 10 represented in FIG. 6.

FIG. 7 shows a representation of a low-pass filter implementation of a switch circuit, according to one or more embodiments of the invention.

Specifically, FIG. 7 shows an example mode for implementing a communication and sensing circuitry for simultaneous sensing and data communication of an implantable medical device 10 with an external device 12. The implementation of the switch circuit of the implantable medical device 10 is similar to the implementation of FIG. 6, but utilizes a low-pass filter at an electrogram amplifier front-end of the sense/pace circuitry 46 of the implantable medical device 10. In at least one embodiment, a filter capacitor 17 may be electrically connected in series to the switch 16 and a filter resistor 15 may be electrically connected in parallel to the switch 16. The filter capacitor 17, in embodiments of the invention, may act to maintain the DC voltage on the electrodes 18 and 18' because it may be continually charged by the filter resistor 15 bypassing the switch 16, when the switch 16 is open. The filter resistor 15, in at least one embodiment, with preferably about 39 kOhm and filter capacitor 17, with preferably about 33 nF, may act as a low-pass filter with a cutoff frequency of preferably about 124 Hz. The filter may prevent high frequency noise from entering the electrogram amplifier. When the at least one switch 16 is closed, in embodiments of the invention, the filter resistor 15 may be shorted to low impedance and most of the input voltage may fall across the filter capacitor 17. By way of one or more embodiments, the cutoff frequency (filter corner) may be shifted to a higher frequency of about 300 kHz depending on the switch impedance. The high frequency carrier signal may be shunted through the filter capacitor 17 to the other electrode 18. The at least one switch 16 in this configuration may allow sensing of low frequency electrocardiograms while shunting high frequency carrier signals from one electrode, e.g., the tip electrode 18 to the other electrode, e.g., the ring electrode 18', in at least one embodiment. This shunting of the high frequency may alter the local electric field around the implantable medical device 10 allowing communication.

Charge injection by the at least one switch 16, in one or more embodiments, may cause slight noise on the electrogram sensing. In one or more embodiments there is a trade-off between charge injection and switch impedance. If charge injection by the at least one switch 16 is high, in embodiments of the invention, the charge may be deposited on the filter capacitor 17 and the electrodes 18 and may cause switching artifact. The electrogram may nonetheless be acquired but high frequency noise may be present. In at least one embodiment, switch impedance may affect the amplitude of the reflected signal to the external device 12. The higher the impedance the lower the reflected signal. Therefore, in one or more embodiments, the ideal at least one switch 16 has low charge injection and low impedance.

In at least one embodiment, a plurality of filter resistors 15 may be used. In this case filter resistor 15 may be formed by a plurality of resistors that may be connected by additional switches in parallel to the at least one switch 16. In one or more embodiments, different values of filter resistor 15 may be used. For example, if two different values for resistor 15 are used, two bit of information may be transmitted in parallel, e.g. at least one switch 16 may open and low value of resistor 15 represent 00, at least one switch 16 open and high value of resistor 15 represents 01, at least one switch 16 closed and low value of resistor 15 represents 10 and at least one switch 16 closed and high value of resistor 15 represents 11.

Figure 8:
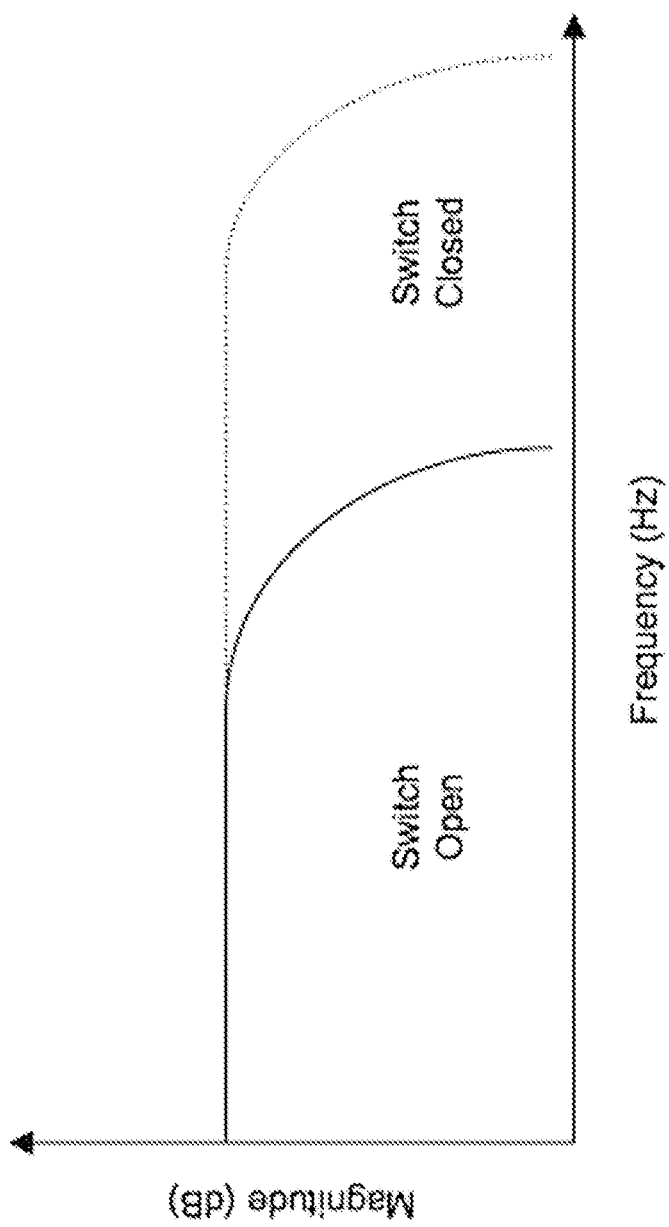
FIG. 8 shows a diagram illustrating the change of the frequency response and in particular the low-pass filter cutoff frequency (corner) change during transmission, according to one or more embodiments of the invention.

FIG. 8 shows a diagram illustrating the change of the frequency response and in particular the low-pass filter cutoff frequency (corner) change during transmission, according to one or more embodiments of the invention.

Specifically, in FIG. 8, the diagram of the magnitude in dB in dependence of the frequency in Hz illustrates the change of the frequency response due to switching the switch 16. The low-pass filter cutoff frequency (corner), in at least one embodiment, may change during transmission, when the at least one switch 16 is changed from an open to a closed position. Preferably, in embodiments of the invention, the low-pass filter cutoff frequency may be in the range of 100 to 200 Hz, most preferably about 124 Hz in an open state. The low-pass filter may be used to prevent high frequency noise from entering the amplifier in at least one embodiment. Switching the at least one switch 16 may shift the cutoff frequency (corner) to a higher frequency in dependence of the switch impedance, e.g., to about 300 kHz in a closed state of the at least one switch 16.

FIGS. 9 and 10 illustrate a simulation of passive impedance-based data communication. Specifically, FIG. 9 shows a circuit diagram for a simulation scenario for simulating impedance change based data communication, according to one or more embodiments of the invention, and FIG. 10 shows a plot illustrating a simulation result achieved by using the diagram depicted in FIG. 9, according to one or more embodiments of the invention.

Figure 11A:
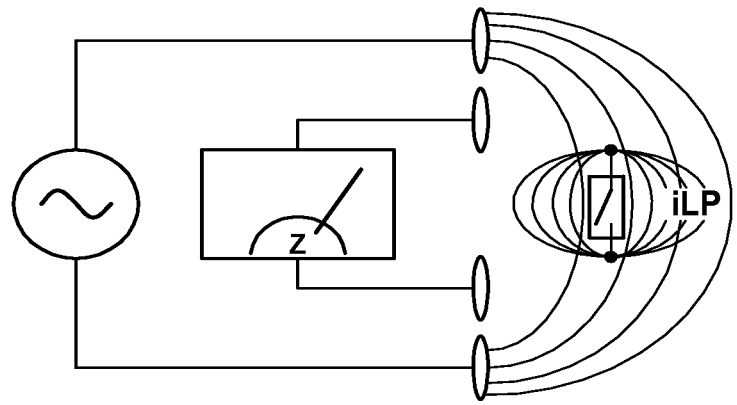
FIG. 11A shows a representation of communication between the implantable medical device and an external device showing the imparted oscillatory field and the local oscillatory field being modulated by the implantable medical device, according to one or more embodiments of the invention.

FIG. 11A shows a representation of communication between the implantable medical device and an external device showing the imparted oscillatory field and the local oscillatory field being modulated by the implantable medical device, according to one or more embodiments of the invention.

Figure 11B:
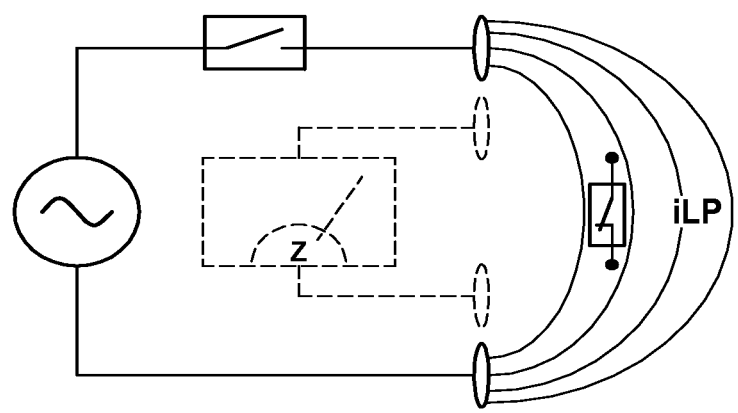
FIG. 11B shows a representation of communication between the external device and the implantable medical device, according to one or more embodiments of the invention.

FIG. 11B shows a representation of communication between the external device and the implantable medical device, according to one or more embodiments of the invention.

Figure 12:
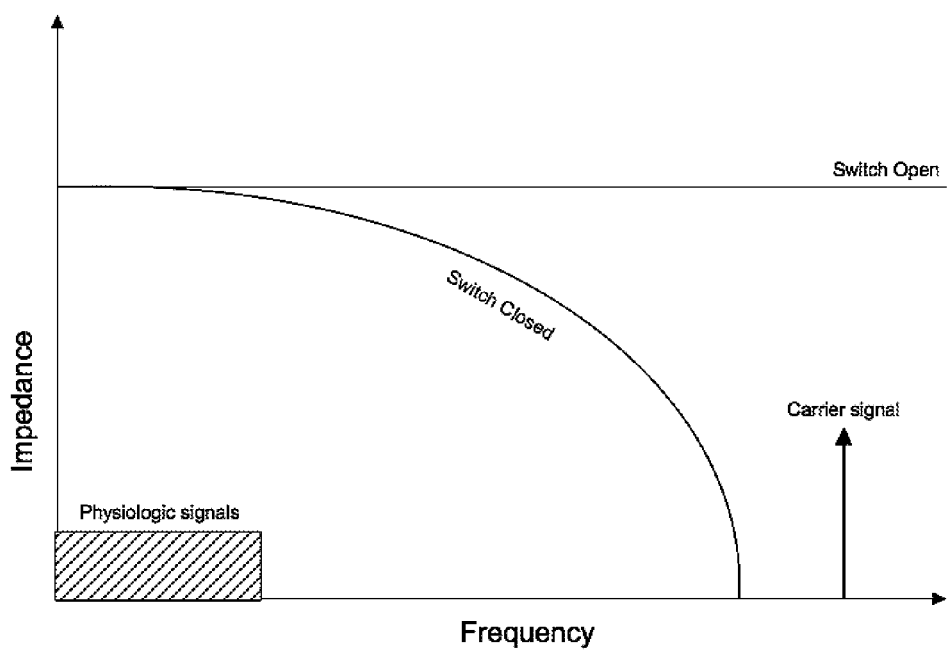
FIG. 12 shows the change of impedance across the implantable medical device when the modulating switch is open and closed, according to one or more embodiments of the invention.

FIG. 12 shows the change of impedance across the implantable medical device when the modulating switch is open and closed, according to one or more embodiments of the invention.

Standard electrode-electrolyte-body impedance models and blood impedance models, in embodiments of the invention, were combined with a lock-in demodulator in a model of the passive impedance implementation of the invention. Each simulation component, in embodiments of the invention, is labeled, with the 'device' modeled in a box labeled with "10" with access impedance and four closing switches to simulate the communication of two data bits to the external receiver/demodulator. In at least one embodiment, environmental and breathing noise may be induced in the model with voltage sources V3, V4, and V5 simulating line noise, rf noise, and breathing, body changing impedance noise, respectively.

The simulation signal at output filter resistor R21, in at least one embodiment, is shown as the trace in FIG. 10. The impedance changes, in embodiments of the invention, may be at a detectable level (showing 2 bits) beyond the background noise that has been filtered out due to the lock-in receiver system. The slope to the left of this plot shows the final settling time of the filters.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable device comprising:
    a data communication device,
        wherein said data communication device comprises a device configured to alter an oscillatory electric field imposed on a conductive medium surrounding the implantable device,
        wherein the device configured to alter an oscillatory electric field is further configured to modulate an impedance of a volume of body tissue surrounding the implantable device when the implantable device is in its implanted state and within an oscillatory electric field, and
        wherein the device that alters an oscillatory electric field comprises a field generating device configured to generate an oscillatory electric field that is phase-synchronized with an oscillatory electric field imposed on a conductive medium surrounding the implantable device; and,
    at least one switch and at least two electrodes connected to the at least one switch,
        wherein the at least two electrodes are configured to be electrically connected and disconnected, respectively, in an alternating manner by the at least one switch according to a code, and
        wherein said code represents data configured to be transmitted from the implantable medical device to an external device.

2. The implantable device according to claim 1, wherein the at least two electrodes are further configured to cause a change of impedance of the conductive medium when the at least two electrodes are connected and disconnected, respectively, in an alternating manner by the at least one switch.

3. The implantable device according to claim 2, wherein the at least one switch is configured to alternate the impedance between the at least two electrodes such that the oscillatory electric field is modulated and low frequency signals are not modulated.

4. The implantable device according to claim 3, wherein the implantable device further comprises a capacitor electrically connected in series with the at least one switch and between the two at least two electrodes and a resistor electrically connected in parallel with the at least one switch.

5. The implantable device according to claim 2, further comprising a switch control, wherein the at least one switch is connected to the switch control, and wherein the switch control is configured to sense an oscillatory electric field imposed on a conductive medium surrounding the implantable device.

6. The implantable device according to claim 5, wherein the switch control comprises a phase-locked loop (PLL) and a frequency divider, wherein the phase-locked loop is configured to lock in a frequency of an oscillatory electric field imposed on a conductive medium surrounding the implantable device, and wherein the frequency divider is connected to the phase-locked loop and is configured to divide a frequency signal outputted by the phase-locked loop.

7. The implantable device according to claim 6, wherein the switch control comprises a band-pass filter, and wherein the band-pass filter is configured to filter a signal fed to the phase-locked loop.

8. The implantable device according to claim 5, wherein the switch control is connected to the at least two electrodes and is configured to sense an oscillatory electric field imposed on a conductive medium via the at least two electrodes.

9. The implantable device according to claim 1, further comprising a field generation controller operatively connected to the field generating device and is configured to control the field generating device in response to an oscillatory electric field imposed on a conductive medium surrounding the implantable device.

10. A data communication system comprising:
an implantable device; and,
an external device that comprises or is connected to at least two surface electrodes,
wherein the implantable device comprises
a data communication device,
wherein said data communication device comprises a device configured to alter an oscillatory electric field imposed on a conductive medium surrounding the implantable device,
wherein the device configured to alter an oscillatory electric field is further configured to modulate an impedance of a volume of body tissue surrounding the implantable device when the implantable device is in its implanted state and within an oscillatory electric field, and
wherein the device that alters an oscillatory electric field comprises a field generating device configured to generate an oscillatory electric field that is phase-synchronized with an oscillatory electric field imposed on a conductive medium surrounding the implantable device; and,
at least one switch and at least two electrodes connected to the at least one switch,
wherein the at least two electrodes are configured to be electrically connected and disconnected, respectively, in an alternating manner by the at least one switch according to a code, and
wherein said code represents data configured to be transmitted from the implantable medical device to the external device; and,
wherein the external device further comprises
an external field generator configured to generate an oscillatory electric field to be imposed on a body via the at least two surface electrodes, and
at least one sensor configured to sense alterations of impedance and/or an oscillatory electric field generated by the implantable device.

11. The data communication system according to claim 10, wherein the external device further comprises a lock-in amplifier, an amplitude modulation (AM) demodulator configured to demodulate amplitude-modulated signals and an analog-to-digital converter, wherein the analog-to-digital converter is operatively connected to the AM demodulator and the lock-in amplifier, and wherein the analog-to-digital converter is configured to output a signal that represents a signal transmitted by the implantable device.

12. The data communication system according to claim 11, wherein the external device is further configured to encode the demodulated amplitude-modulated signals according to an encoding scheme, wherein the encoding scheme comprises a logical 1 to modulate the at least one switch as closed-open-closed-open and a logical 0 to modulate the at least one switch as open-closed-open-closed, and wherein via the encoding scheme the at least one switch is either closed or open twice as long when transitioning from logical 0 to logical 1 or from logical 1 to logical 0.

* * * * *